US010391048B2

(12) United States Patent
Meng

(10) Patent No.: US 10,391,048 B2
(45) Date of Patent: Aug. 27, 2019

(54) RECOMBINANT HIGH-STABILITY SUPEROXIDE DISMUTASE AND APPLICATION THEREOF

(71) Applicant: Hangzhou Redox Pharmatech Co., Ltd., Jiande, Zhejiang (CN)

(72) Inventor: Fanguo Meng, Zhejiang (CN)

(73) Assignee: Hangzhou Redox Pharmatech Co., Ltd., Jiande, Zhejiang (CN)

( * ) Notice: Subject to any disclaimer, the term of this patent is extended or adjusted under 35 U.S.C. 154(b) by 0 days.

(21) Appl. No.: 15/767,991

(22) PCT Filed: Dec. 26, 2016

(86) PCT No.: PCT/CN2016/112123
§ 371 (c)(1),
(2) Date: Apr. 12, 2018

(87) PCT Pub. No.: WO2017/143850
PCT Pub. Date: Aug. 31, 2017

(65) Prior Publication Data
US 2018/0303743 A1  Oct. 25, 2018

(30) Foreign Application Priority Data
Feb. 23, 2016 (CN) .......................... 2016 1 0099824

(51) Int. Cl.
| | |
|---|---|
| *A61K 8/66* | (2006.01) |
| *A61K 38/44* | (2006.01) |
| *A61Q 19/08* | (2006.01) |
| *C12N 15/63* | (2006.01) |
| *A61P 29/00* | (2006.01) |
| *A61Q 19/02* | (2006.01) |
| *A23L 29/00* | (2016.01) |

(52) U.S. Cl.
CPC ................ *A61K 8/66* (2013.01); *A23L 29/06* (2016.08); *A61K 38/44* (2013.01); *A61K 38/446* (2013.01); *A61P 29/00* (2018.01); *A61Q 19/02* (2013.01); *A61Q 19/08* (2013.01); *C12N 15/63* (2013.01); *C12Y 115/01001* (2013.01); *Y02A 50/402* (2018.01)

(58) Field of Classification Search
None
See application file for complete search history.

(56) References Cited

FOREIGN PATENT DOCUMENTS

| | | |
|---|---|---|
| CN | 101275144 | 10/2008 |
| CN | 101985614 | 3/2011 |
| CN | 105624126 | 6/2016 |
| JP | 2008005797 | 1/2008 |

OTHER PUBLICATIONS

International Search Report for PCT/CN2016/112123 dated Mar. 31, 2017 with English translation (10 pages).

*Primary Examiner* — Suzanne M Noakes
(74) *Attorney, Agent, or Firm* — Sheppard Mullin Richter & Hampton LLP

(57) ABSTRACT

The invention discloses a novel high-temperature resistant superoxide dismutase (SOD) and a coding gene and application thereof. The superoxide dismutase has a very high stability and activity under various severe conditions such as high temperature, high acidity or alkalinity and various proteases such as pepsin and trypsin. The superoxide dismutase of the present invention overcomes the problems of the existing SOD products, such as unstability, low in activity or even a complete lack of activity and prone to degradation and inactivation in the digestive tract. And the superoxide dismutase of the present invention is expected to be developed into cosmetics or health-care foods or medicines which are stable in activity and have a good effect.

19 Claims, 9 Drawing Sheets
Specification includes a Sequence Listing.

Compared with the model control group, *** p <0.001.

Compared with the model control group, *** p <0.001.

Compared with the model control group, *** p <0.001.

Compared with the model control group, * p <0.05  p <0.01 * p <0.001.

Compared with the model control group, * p <0.05  p <0.01 * p <0.001.

SEQUENCE LISTING

<160> NUMBER OF SEQ ID NOS: 4

<210> SEQ ID NO 1
<211> LENGTH: 28
<212> TYPE: DNA
<213> ORGANISM: artificial sequence
<220> FEATURE:
<223> OTHER INFORMATION: thermophilic bacteria HB27 SOD forward primer

<400> SEQUENCE: 1
aagaattcat gccgtacccg ttcaagct                                28

<210> SEQ ID NO 2
<211> LENGTH: 27
<212> TYPE: DNA
<213> ORGANISM: artificial sequence
<220> FEATURE:
<223> OTHER INFORMATION: thermophilic bacteria HB27 SOD reverse primer

<400> SEQUENCE: 2
ctgtcgactc aggctttgtt gaagaac                                 27

<210> SEQ ID NO 3
<211> LENGTH: 615
<212> TYPE: DNA
<213> ORGANISM: artificial sequence
<220> FEATURE:
<223> OTHER INFORMATION: nucleotide sequence of M-type SOD encoding gene

<400> SEQUENCE: 3
atgccgtacc cgttcaagct tcctgaccta ggctacccct acgaggccct cgagccccac    60
attgacgcca agaccatgga gatccaccac cagaagcacc acggggccta cgtgacgaac   120
ctcaacgccg ccctggagaa gtaccectac ctccacgggg tggaggtgga ggtcctcctg   180
aggcacctcg ccgcccttcc ccaggacatc cagaccgccg tgcgcaacaa cggggggcggg   240 cacctgaacc acagcctctt ctggaggctc ctcaccccg gggggccaa ggagcccgtg     300 ggggagctga agaaggccat tgacgagcag ttcgggggct tccaggccct caaggagaag   360
ctcacccagg cggccatggg ccggttcggc tcgggctggg cctggctcgt gaaggacccc   420
ttcggcaagc tccacgtcct ctccaccccc aaccaagaca ccccgtgat ggagggcttc    480 acccccatcg tgggcattga cgtctgggag cacgcctact acctcaagta ccagaaccgc   540
cgggccgatt acctccaggc catctggaac gtcctcaact gggacgtggc cgaggagttc   600
ttcaataaag cctga                                                   615

<210> SEQ ID NO 4
<211> LENGTH: 204
<212> TYPE: PRT
<213> ORGANISM: artificial sequence
<220> FEATURE:
<223> OTHER INFORMATION: amino acid sequence of M-type SOD

<400> SEQUENCE: 4

Met Pro Tyr Pro Phe Lys Leu Pro Asp Leu Gly Tyr Pro Tyr Glu Ala
1               5                   10                  15

Leu Glu Pro His Ile Asp Ala Lys Thr Met Glu Ile His His Gln Lys
            20                  25                  30

His His Gly Ala Tyr Val Thr Asn Leu Asn Ala Ala Leu Glu Lys Tyr
        35                  40                  45

Pro Tyr Leu His Gly Val Glu Val Glu Val Leu Leu Arg His Leu Ala
    50                  55                  60

```
Ala Leu Pro Gln Asp Ile Gln Thr Ala Val Arg Asn Asn Gly Gly Gly
65                  70                  75                  80

His Leu Asn His Ser Leu Phe Trp Arg Leu Leu Thr Pro Gly Gly Ala
                85                  90                  95

Lys Glu Pro Val Gly Glu Leu Lys Lys Ala Ile Asp Glu Gln Phe Gly
            100                 105                 110

Gly Phe Gln Ala Leu Lys Glu Lys Leu Thr Gln Ala Ala Met Gly Arg
            115                 120                 125

Phe Gly Ser Gly Trp Ala Trp Leu Val Lys Asp Pro Phe Gly Lys Leu
    130                 135                 140

His Val Leu Ser Thr Pro Asn Gln Asp Asn Pro Val Met Glu Gly Phe
145                 150                 155                 160

Thr Pro Ile Val Gly Ile Asp Val Trp Glu His Ala Tyr Tyr Leu Lys
                165                 170                 175

Tyr Gln Asn Arg Arg Ala Asp Tyr Leu Gln Ala Ile Trp Asn Val Leu
                180                 185                 190

Asn Trp Asp Val Ala Glu Glu Phe Phe Asn Lys Ala
            195                 200
```

RECOMBINANT HIGH-STABILITY SUPEROXIDE DISMUTASE AND APPLICATION THEREOF

CROSS REFERENCE TO RELATED APPLICATIONS

The present application is a national stage application of International Application PCT/CN2016/112123, filed Dec. 26, 2016, which claims the benefit of Chinese Patent Application No. 201610099824.8 filed Feb. 23, 2016, the contents of which are incorporated by reference in their entireties into the present disclosure.

FIELD OF THE INVENTION

The present invention relates to the field of biomedical, cosmetic and functional food etc, and more particularly to a superoxide dismutase (SOD) which is resistant to digestive enzymes, acid and alkali, and high temperature, and its coding genes and applications, and cosmetics, health food and pharmaceutical compositions comprising the high temperature resistant superoxide dismutase and applications thereof.

BACKGROUND OF THE INVENTION

Free radicals are hotspot in the research of life sciences. In 1956, Harman of the United States introduced the concept of free radicals in radiation chemistry into the field of biology and proposed the famous free radial theology. Reactive oxygen species (ROS) is the most common free radical in the body. The free radicals in the human body are mainly oxygen free radicals. Excessive reactive oxygen species in the body can cause lipid peroxidation, change biofilm structures and functions, cause protein denaturation, cross-linking, enzyme inactivation and so on. Reactive oxygen species is closely related to the occurrence and development of myocardial shock, radiation injury, atherosclerosis, immune system defects and other diseases. Excessive free radicals induce oxidation reaction in organism, damage the body's tissues and cells, and then lead to aging, so Harman proposed the famous free radical theory of aging. Oxidative stress leads to oxidative damage of biomolecules, causing endogenous damage associated molecular patterns (DAMPs) to produce and release cytokines. Cytokines can activate signaling pathways downstream of pattern recognition receptors (PRRs) such as nuclear factor κB (NF-κB), JAK, STAT and MAPK and so on, leading to increased cytokines and chemokines release, recruitment and activation of more inflammation cells, causing systemic chronic inflammatory response. Based on the tight relationship between oxidative stress and inflammation, aging, De la Fuente et al. proposed the oxidation-inflammatory aging theory and thought that oxidative stress leads to inflammatory aging.

Superoxide dismutase is widely found in various organisms, an indispensable, important oxygen free radical scavenger in body, and plays an important role in the biological defense of oxidative damage. Depending on the combined metal ions, SOD can be divided into four categories: Cu/Zn-SOD, Fe-SOD, Mn-SOD and Ni-SOD. Studies have shown that SOD can remove oxygen free radicals effectively, treat a variety of inflammation, and also play an important role in the prevention and treatment of radiation damage. Wherein, the Mn-SOD is the most stable, with the minimal toxicity.

In the oxidized and phosphorylated electron transport system of mitochondria, the molecule $O_2$ is the last receptor. In normal circumstances $O_2$ receives four electrons and turns into $H_2O$. If part of the electrons are transferred, a highly active oxygen free radical (ROS) is formed, and the oxygen free radical attacks lipid membrane, protein, DNA, causing neurodegeneration, aging, cancer, pulmonary fibrosis, vascular disease. ROS is also an important factor in the induction of inflammatory response. Inflammation is the body's defensive response to infection source, trauma, or tissue ischemia. Abnormal inflammatory response causes a variety of diseases. The most common pathological features of inflammation are the migration, aggregation and infiltration of leukocytes (neutrophils and macrophages). The research of the location and number of neutrophils is the most common method of studying inflammation. Many experiments have shown that antioxidant enzymes are the main regulator of inflammatory response. Mn-SOD in mitochondria is the first enzyme to remove oxygen free radicals, and its activity relates to the scavenging rate of free radical and the repair efficiency of inflammation.

Mammalian Mn-SOD is located in the mitochondria, and its function is to control the mitochondrial $O_2^-$ level, to avoid the damage of oxygen free radical to mitochondria. Studies on the function of Mn-SOD in vivo have shown that Mn-SOD is closely related to inflammatory response and cell senescence. The mitochondria in most of the mice lacking the gene have serious damage. After the gene is knocked out, the mice often die in the fetal phase, while supplementation with Mn-SOD can prolong the survival time. Mn-SOD may become a new anti-inflammatory drug.

Environmental pollution, psychological stress, addiction to tobacco and alcohol and other bad habits will lead to abnormal metabolism in the body. A large number of oxygen free radicals accumulation leads to depression, fatigue, reduced immunity, causing a sub-health state for a long time. If one can supplement adequate amount of SOD, these sub-health symptoms will be improved. Therefore, SOD can be used for health care products or as food additives. In addition, Mn-SOD also has a role in the anti-aging, prevention of skin pigmentation, which can also be added and applied in cosmetics.

Although the current basic research has proved the action mode of SOD and its effect, but SOD is still difficult to be practically applied, and cannot achieve the desired therapeutic efficiency. This is mainly caused by the following factors: firstly, due to the procedure of drug preparation, cosmetics and food processing usually involves the steps of sterilization, heating extraction and so on, while the characteristics of ordinary SOD are poor stability, high temperature intolerant, long-term storage intolerant, which seriously constrain its industrial applications; secondly, SOD is a biological macromolecular, the transdermal absorption amount is limited, thus its efficacy may be limited; finally, both oral drugs and food are digested and absorbed through the digestive tract, SOD as a kind of protein is often digested and degraded by the protease in gastric juice and intestinal fluid, which cannot play its due effect. The European Food Safety Authority (EFSA) argues that more evidences are needed for the role of SOD in promoting health (EFSA Journal 2010; 8 (10): 1753).

Although many researchers have also explored a number of studies, such as the production of high temperature resistant SOD using genetic engineering methods in order to overcome these deficiencies. So far, the following technical problems have not been overcome in the prior art: 1) recombinant SOD is insufficient in resistance to acid and alkali; 2) the produced SOD is easily degraded by the pepsin and trypsin in the digestive tract and losses activity.

Therefore, the deficiency of the prior SOD in resistance to high temperature, acid and alkali, pepsin and trypsin degradation greatly limits the application of SOD in the fields of cosmetics, food and medicine. It is urgent to develop a new superoxide dismutase that is resistant to high temperature, acid and alkali, pepsin and trypsin degradation simultaneously.

SUMMARY OF THE INVENTION

The present invention solves the above-mentioned problems existed in the prior art by means of genetic engineering, and therefore one object of the present invention is to provide a novel superoxide dismutase resistant to high temperature, acid and alkali and degradation of digestive tract enzymes, and its coding gene and application thereof.

The present invention provides a superoxide dismutase resistant to high temperature, acid and alkali, and degradation of digestive tract enzymes, and the amino acid sequence thereof is shown in SEQ ID NO.4.

The present invention also provides a gene encoding the above-mentioned superoxide dismutase resistant to high temperature, acid and alkali, and degradation of digestive tract enzymes, and preferably the gene sequence is the DNA sequence shown in SEQ ID NO.3 in the Sequence Listing.

According to another aspect of the present invention, the present invention also provides an expression vector, a transgenic cell line, and a host bacterium comprising the above-described gene.

According to another aspect of the present invention, the present invention also provides a pharmaceutical composition comprising a therapeutically effective amount of superoxide dismutase with its amino acid sequence as shown in SEQ ID NO: 4. Wherein, "therapeutically effective amount" means an effective amount of the pharmaceutical composition disclosed herein that is effective at the desired dose or time period required to achieve the desired result or therapeutic outcome. The therapeutically effective amount may vary depending on factors known in the art, such as the disease status, age, gender, and weight of the person or animal to be treated. It will be appreciated by those skilled in the art that the dosage regimen may be altered to provide an optimal therapeutic response. For example, a number of separate doses may be administered daily or a proportionally reduced dose may be administrated due to the urgency of the treatment condition. In addition, the compositions of the present disclosure may be administered at a desired frequency to achieve a therapeutically effective amount.

According to another aspect of the present invention, the pharmaceutical composition of the present invention further comprises an antibacterial agent and/or a pharmaceutically acceptable carrier and/or excipient. The dosage form of the pharmaceutical composition is an oral dosage form or an external dosage form, wherein the oral dosage form is preferably an oral solution, a tablet, a pill, a capsule, granules and oral powders; the external dosage form is preferably external powders, ointment, patch, external liquid agent, suppository, spray, aerosol, inhalant. In addition, in order to prolong the retention time of the protein drug in the blood, the present invention can also chemically modify the high temperature resistant SOD with a conventional modifying agent such as fatty acids, polysaccharides, lauroyl chloride, dextran, polyethylene glycol (PEG) and the like.

According to another aspect of the present invention, there is also provided a cosmetic composition, wherein the cosmetic composition comprises an effective amount of the superoxide dismutase of the present invention.

According to another aspect of the present invention, there is also provided a food additive comprising the superoxide dismutase of the present invention.

According to another aspect of the present invention, there is provided a process for the preparation of a high temperature resistant superoxide dismutase with the amino acid sequence as set forth in SEQ ID NO: 4, wherein the preparation method comprises, expressing a nucleic acid sequence encoding the high temperature resistant superoxide dismutase, such as the DNA sequence shown in SEQ ID NO.3 in the Sequence Listing or obtaining the high temperature resistant superoxide dismutase by the chemical synthesis method.

According to another aspect of the present invention, the present invention also provides the use of said superoxide dismutase or said gene or said expression vector, transgenic cell line, host bacterium or said pharmaceutical composition according to the invention in preparation of anti-inflammatory drugs. Wherein, the inflammation comprises: mucosal inflammation, inflammation caused by exogenous inflammatory factors, or skin inflammation. Wherein, the mucosal inflammation comprises: mucosal inflammations of respiratory tract, digestive tract, reproductive organs, auditory organs, visual organs, preferably oral ulcer, gingivitis, enteritis, gastritis, vaginitis, pelvic Inflammation, cystitis, cervicitis, rhinitis, pharyngitis, otitis media, otitis externa, eye conjunctivitis, eye keratitis; the inflammation caused by exogenous inflammatory factors includes an inflammation caused by biological factors, physical factors, exogenous chemical factors, or a combination thereof; preferably, the inflammation caused by the biological factors includes inflammation caused by bacteria, virus, rickettsia, protozoon, fungi, spirochete and parasite acting on the body; preferably, the inflammation caused by the physical factors include an inflammation caused by mechanical force, high temperature, low temperature, ionizing radiation, ultraviolet radiation acting on the body, more preferably an inflammation caused by burn, scald, frostbite, sunburn, cut, radiation damage, or an inflammation formed after surgery and radiotherapy; preferably, the inflammation caused by the exogenous chemical factors includes an inflammation caused by radioactive material, strong acid, strong base, strong oxidant, alcohol, chemical drug acting on the body, more preferably alcohol or drug-induced hepatitis, inflammation formed after chemotherapy; the skin inflammation includes tinea manus and pedis, folliculitis, contact dermatitis, eczema, urticaria, neurodermatitis, seborrheic dermatitis, preferably infant eczema.

Specifically, the biological factor is the most common cause of inflammation, and the inflammation caused is also known as infection. For example, bacteria can release endotoxin and exotoxin to stimulate inflammation; virus can cause cell necrosis of the infected cells by replication in the cell; some pathogens can induce hypersensitivity inflammation through its antigenicity, such as tuberculosis. Among them, the physical factors including mechanical factors (such as cutting), high temperature (such as burn, scald), low temperature (such as frostbite), ionizing radiation (such as nuclear radiation damage), ultraviolet (such as UV damage) which act on the human body, and can cause inflammation as long as reach a certain intensity or a certain action time. Among them, exogenous chemical factors include radioactive substances, strong acids, strong bases, strong oxidants or other chemicals, which can cause inflammation as long as reach a certain concentration or dose.

According to another aspect of the present invention, the present invention also provides the use of the superoxide dismutase or said gene or said expression vector, transgenic cell line, host bacteria of the present invention in the preparation of cosmetics and health food products. Among them, cosmetics are preferably anti-aging, skin pigmentation preventing cosmetics.

DETAILED DESCRIPTION OF THE INVENTION

Figure 1:
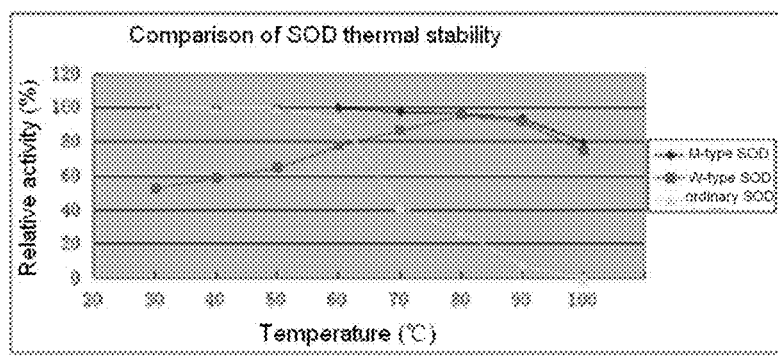
FIG. 1 is a comparison chart of the thermal stability of the wild-type high temperature resistant SOD, mutant high temperature resistant SOD and ordinary SOD.

Example 1. Preparation of Mutant High Temperature Resistant Superoxide Dismutase of the Present Invention 1. The Mutant High Temperature Resistant SOD Strain with a High Yield was Obtained The target gene was amplified with the following primer sequences using the gene encoding SOD in the thermophilic bacteria HB27 (purchased from the American ATCC cell bank) as the template: Forward primer: 5'-AAGAATTCAT-GCCGTACCCGTTCAAGCT-3' (SEQ ID NO.1); Reverse primer: 5'-CTGTCGACTCAGGCTTTGTTGAAGAAC-3' (SEQ ID NO. 2). The amplified product was recovered using a extraction kit (purchased from Sangon Biotech (Shanghai) Co., Ltd.), digested with enzymes (EcoRI and SalI) and ligated to the plasmid vector (pET28a (+), purchased from Sangon Biotech (Shanghai) Co., Ltd.) which was also digested with the same enzymes, then the recombinant plasmid was transformed into the competent E. coli BL21 (DE3) (purchased from Sangon Biotech (Shanghai) Co., Ltd.). The strain of mutant high temperature resistant SOD with a high-yield (hereinafter referred to as M-type SOD) was obtained by screening and sequencing, and the specific nucleotide sequence of the M-type SOD encoding gene were sequenced as:

(SEQ ID NO. 3)
```
 1   ATGCCGTACCCGTTCAAGCTTCCTGACCTAGGCTACCCCTACGAGGCCCTCGAGCCCCAC

61   ATTGACGCCAAGACCATGGAGATCCACCACCAGAAGCACCACGGGGCCTACGTGACGAAC
```

```
121    CTCAACGCCGCCCTGGAGAAGTACCCCTACCTCCACGGGGTGGAGGTGGAGGTCCTCCTG

181    AGGCACCTCGCCGCCCTTCCCCAGGACATCCAGACCGCCGTGCGCAACAACGGGGGCGGG

241    CACCTGAACCACAGCCTCTTCTGGAGGCTCCTCACCCCCGGGGGGCCAAGGAGCCCGTG

301    GGGGAGCTGAAGAAGGCCATTGACGAGCAGTTCGGGGGCTTCCAGGCCCTCAAGGAGAAG

361    CTCACCCAGGCGGCCATGGGCCGGTTCGGCTCGGGCTGGGCCTGGCTCGTGAAGGACCCC

421    TTCGGCAAGCTCCACGTCCTCTCCACCCCCAACCAAGACAACCCCGTGATGGAGGGCTTC

481    ACCCCCATCGTGGGCATTGACGTCTGGGAGCACGCCTACTACCTCAAGTACCAGAACCGC

541    CGGGCCGATTACCTCCAGGCCATCTGGAACGTCCTCAACTGGGACGTGGCCGAGGAGTTC

601    TTCAATAAAGCCTGA
```

2. The Expression and Purification of M-Type SOD

The fermentation process was carried out by four steps of primary seed culture, secondary seed culture, tank fermentation, induction expression, and finally the fermentation product M-type SOD was obtained. The specific process is as follows:

The basic LB medium components of the fermentation tank were formulated, and the supplement ingredients were shown as the table below.

| Ingredient | supplement amount | supplement frequency |
|---|---|---|
| glucose | 80 g | 5 h |
| ammonium sulfate | 20 g | 5 h |
| K$_2$HPO$_4$ | 8 g | 5 h |

(1) Primary seed culture: 20 ml LB liquid culture;

(2) The culture medium was inoculated with 5 μl of glycerol stock and the final concentration of kanamycin was 50 mg/L, 37° C. and 220 rpm, culture for 10 hours;

(3) Secondary seed culture: the bacteria culture in the last step was transferred to 200 ml LB liquid medium, and the final concentration of kanamycin was 50 mg/L, 37° C., 220 rpm, culture for 4 h;

(4) Tank fermentation: 200 ml of secondary seed bacteria culture in the previous step was inoculated into a fermentation tank with a capacity of 6.6 L; fermentation conditions: dissolved oxygen 30%, temperature at 30° C., pH7.0, rotational speed was automatically adjusted between 200 rpm and 800 rpm according to dissolved oxygen;

(5) Add the inducer IPTG with a final concentration of 1 mM when fermentation was carried out for 5-6 hours and the OD600 was about 28; the fermentation were stopped to after 24 hours and the cells were collected by centrifugation;

(6) After centrifugation, the cells were dissolved in Buffer A (10 mM Tris-HCl, pH 8.0); the cells were ultrasonically broken at 300 W ultrasound, and the total time of ultrasound was 45 min;

(7) Heated at 90° C. for 1 h;

(8) After cooled to room temperature, centrifuged at 4° C., 12000 g for 30 min;

(9) Collected the supernatant and added 50% ammonium sulfate to precipitate the enzyme;

(10) Leave at 4° C. for 120 min, centrifuged at 4° C., 12000 g for 30 min;

(11) Dissolve the precipitate and dialyze overnight;

(12) The product after dialysis was subpackaged and dried and made into end product.

Purified M-type-SOD (purity was up to 98%) has the amino acid sequence:

```
                                                              (SEQ ID NO. 4)
  1    MPYPFKLPDLGYPYEALEPHIDAKTMEIHHQKHHGAYVTNLNAALEKYPYLHGVEVEVLL

61    RHLAALPQDIQTAVRNNGGGHLNHSLFWRLLTPGGAKEPVGELKKAIDEQFGGFQALKEK

121    LTQAAMGRFGSGWAWLVKDPFGKLHVLSTPNQDNPVMEGFTPIVGIDVWEHAYYLKYQNR

181    RADYLQAIWNVLNWDVAEEFFNKA
```

The difference between the amino acid sequences of the M-type SOD and the high temperature resistant SOD disclosed in GenBank (GenBank: BAA25701.1, wild-type high temperature resistant SOD, hereinafter referred to as W-type SOD) is that the amino acid at position 202 of the M-type SOD provided by the present invention is mutated from lysine (Lys or K) at the corresponding position of W-type SOD to asparagine (Asn or N).

Example 2. Analysis of the Physicochemical Properties of the Mutant Type High Temperature Resistant Superoxide Dismutase 1. The Comparison of Heat Resistance We have compared the thermal stability of the W-type SOD (Jianguo Liu et al., Extremophiles, 2011: 15: 221 226, the same below), the M-type SOD provided by the present invention and the ordinary SOD (Sigma, MFCD00132404) (the experiment conditions are the same with that in Jianguo Liu et al., Extremophiles, 2011: 15: 221 226, i.e. treated at different temperatures for 1 hour to measure the remaining enzyme activity). The results were shown in FIG. 1. It can be seen that the M-type SOD provided by the present invention maintained extremely high stability within a wider temperature range.

Figure 2:
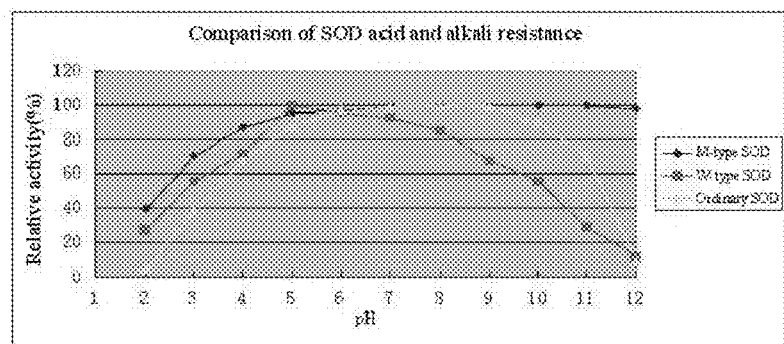
FIG. 2 is a comparison chart of the acid and alkali resistance of the wild-type high temperature resistant SOD, mutant high temperature resistant SOD and ordinary SOD.

2. PH Resistance Comparison:

We compared the stability of W-type SOD, M-type SOD and ordinary SOD (Sigma, MFCD00132404) at different pH (exactly the same conditions as described in Jianguo Liu et al., Extremophiles, 2011: 15: 221 226). The results are shown in FIG. 2.

It can be seen that M-type SOD kept 97% activity at pH 12, while W-type SOD only kept less than 40% activity at pH 11, showing that the M-type SOD has a very prominent acid and alkaline resistance.

3. The Pepsin Resistance Test:

Preparation of simulated gastric fluid: in accordance with the standard of the Pharmacopoeia 2010, namely: take dilute hydrochloric acid 16.4 ml (dilute hydrochloric acid: diluted hydrochloric acid 234 ml with water up to 1000 ml. The HCl contained in the solution should be 9.5% to 10.5%), add about 800 ml of water and pepsin 10 g (Sinopharm, 20141209) and shake well, then add water up to 1000 ml.

Figure 3:
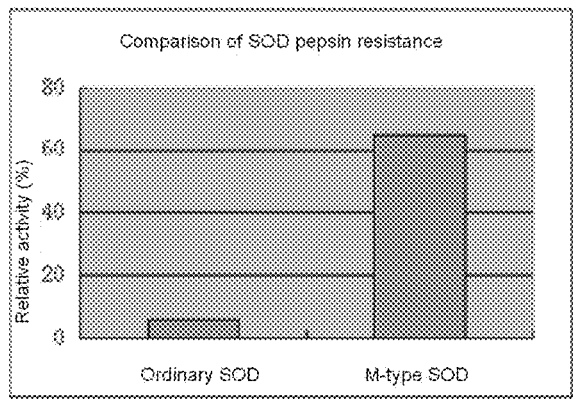
FIG. 3 is a comparison chart of the ability of ordinary SOD and mutant high temperature resistant SOD against pepsin degradation.

SOD is also a protein, which is digested readily by the protease in the digestive tract thus losing activity. After treating both M-type SOD and ordinary SOD enzymes in the above simulated gastric fluid for two hours, it could be found that resistance of M-type SOD against pepsin degradation was significantly better than ordinary SOD, see FIG. 3 for details.

Figure 4:
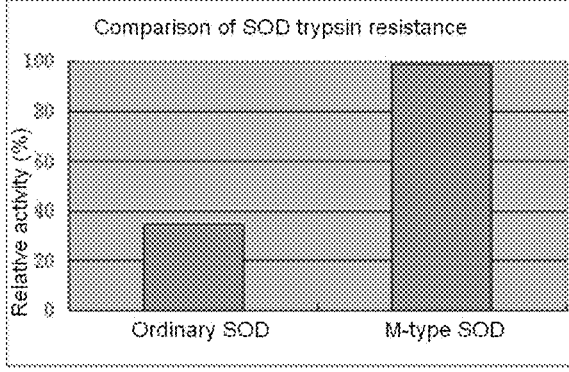
FIG. 4 is a comparison chart of the ability of ordinary SOD and mutant high temperature resistant SOD against trypsin degradation.
Figure 5:
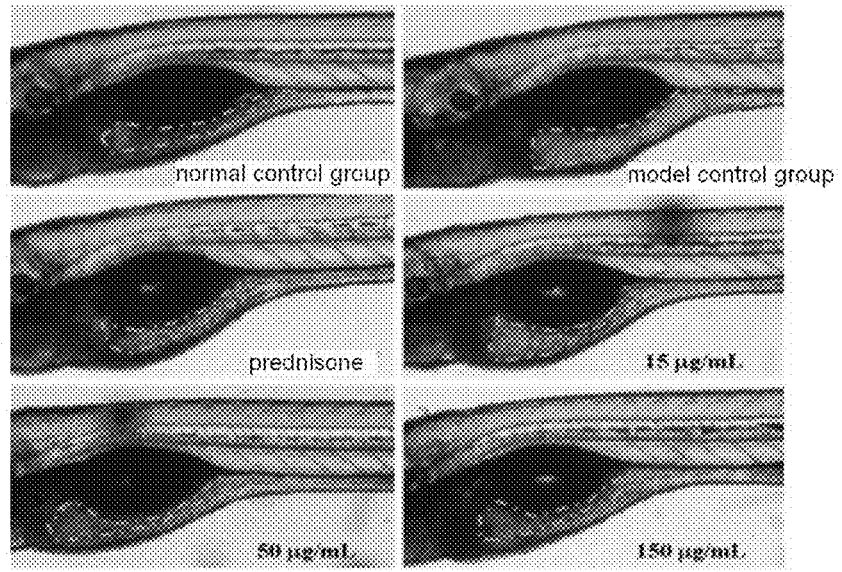
FIG. 5 is a phenotype chart showing the treatment effect of the mutant high temperature resistant SOD on colonitis.
Figure 6:
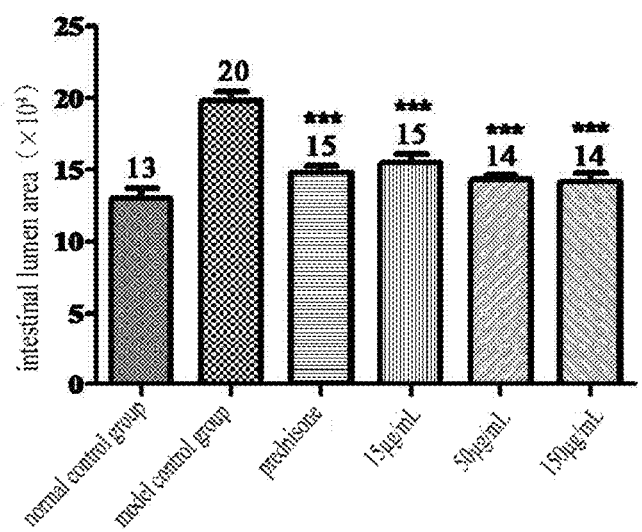
FIG. 6 is a comparison chart showing the treatment effect of the mutant high temperature resistant SOD on the colonitis (intestinal lumen area)
Figure 7:
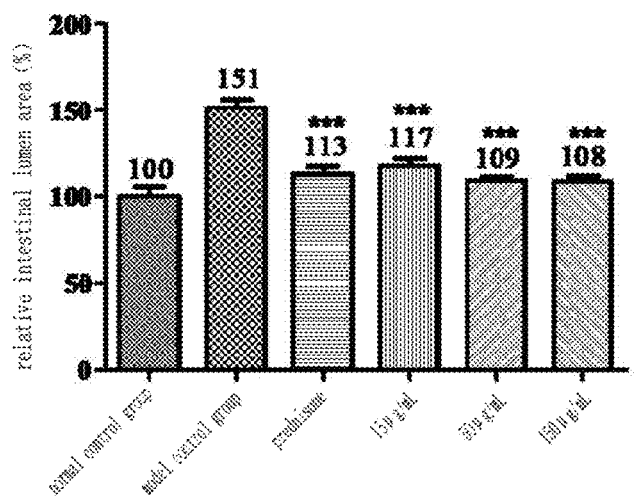
FIG. 7 is a comparison chart showing the treatment effect of the mutant high temperature resistant SOD on the colonitis (relative intestinal lumen area)
Figure 8:
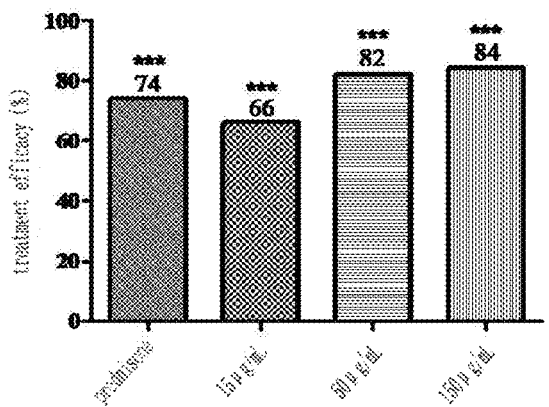
FIG. 8 is a comparison chart showing the treatment efficacy of the mutant high temperature resistant SOD on colonitis.

4. The Trypsin Resistance Test:

The M-type SOD and ordinary SOD are incubated in 10 U/ml 300 U/ml trypsin solution (Shanghai Ruiyong Biotechnology Co. Ltd, RM1021-100 g) at 37° C. for 3 hours, and it was found that M-type SOD did not lose activity, while the ordinary SOD lost nearly 60% activity. This indicates that M-type SOD also has a strong anti-trypsin degradation ability, see FIG. 4 for details.

The enzyme activity of SOD was determined by pyrogallol autoxidation method.

In summary, the mutant SOD (M-type SOD) has the outstanding performance in resistance to high temperature, acid and alkaline changes and digestive enzymes degradation, therefore is expected to be used in oral and external drugs, food and cosmetics, and achieve good therapy, cosmetic and healthy effects.

Example 3. Research of Anti-Mucosal Inflammation of the Mutant High Temperature Resistant Superoxide Dismutase (M-Type SOD) of the Present Invention Experimental Animals:

The zebrafish model is widely used for disease research and drug screening with the following main conditions: (1) a large number of samples can be provided for high-throughput drug screening; (2) high conservation with human in immunology genomics and the like; (3) has a good tracer; (4) can explicitly and clearly demonstrate the most important common pathological features of inflammation. The zebrafish model is one of the most important internationally recognized model animals of drug screening. Zebrafish is transparent and has a strong imaging feature that makes it easier for the researchers to manipulate genes, rendering the animal an ideal model for studying various inflammatory responses. The digestive system of zebrafish is similar to that of mammals, which also contains a liver, pancreas, gallbladder, and a intestinal tract of linear segments with absorption and secretion function. The intestinal epithelium plays a role throughout the intestinal tract and it also contains many epithelial cells that can also be found in mammals, including: absorptive cells, goblet cells, endocrine cells, and the like. Therefore, in recent years zebrafish has become a typical animal model of various inflammatory studies, including mucosal inflammation, especially digestive tract mucosal inflammation, the most representative of which is the zebrafish animal model of inflammatory bowel disease (IBD).

Wild-type (AB) zebrafish (provided by Hunter Biotechnology, Inc) was selected as the experimental animals and in a natural pair of mating breeding mode. A total of 630, each experiment group of 30, with the age of 3 days after fertilization were used for the analysis of M-type SOD on the treatment of colitis and intestinal histopathology. Transgenic neutrophil fluorescent zebrafish (provided by Hunter Biotechnology, Inc) are in a natural pair of mating breeding mode. A total of 210, each experiment group of 30, with the age of 3 days after fertilization were used for the evaluation of M-type SOD on colitis inflammation resolution. The zebrefish was kept in water for fish at 28° C. (Water quality: adding 200 mg instant sea salt per liter reverse osmosis water, conductivity was 480~510 µS/cm, pH: 6.9~7.2; hardness was 53.7~71.6 mg/L CaCO$_3$), experimental animal use license number: SYXK (Zhejiang) 2012-0171. Feed management was in line with international AAALAC certification requirements.

Experimental Drug:

The M-type SOD prepared in Example 1, white powder, was prepared at a concentration of 20 mg/mL with ultrapure water at the time of application as mother solution, fresh made.

Prednisone, white powder, batch number 28778, provided by the Shanghai Crystal Pure Industrial Co., Ltd, was prepared at a concentration of 15 mg/mL with 100% DMSO at the time of application as mother solution.

Trinitrobenzene sulfonic acid (hereinafter referred to as TNBS), brown liquid, batch number D1326018, provided by the Shanghai Crystal Pure Industrial Co., Ltd.

The Instruments Used:

Dissection microscope (SZX7, OLYMPUS, Japan), motorized zoom fluorescence microscopy which can continuously switch magnifications (AZ100, Nikon Corporation); 6-well plates (Nest Biotech); methylcellulose (Aladdin, Shanghai, China).

Model Establishment:

Model 1:

A wild-type (AB) zebrafish of 3 days after fertilization was used to establish a zebrafish colitis model after incubation for 48 h in water for fish containing a final concentration of 4.5 µM TNBS. (Please refer to A. Jemal, R. Siegel, J. Xu, et al. Ward. Clinicians, 2010, 277-300, and Intestinal Upregulation of Melanin-Concentrating Hormone in TNBS-Induced Enterocolitis in Adult Zebrafish. Plos One, 2013, 8(12):1524-1528). The results of the modeling showed that: compared with the normal control group (130711), the intestinal lumen area of the model control group was 197660, p<0.001, indicating that the model was established successfully and used in the following experiment 1.

Model 2:

Transgenic neutrophil fluorescent zebrafish of 3 days after fertilization was used to establish a zebrafish colitis model after incubation for 48 h in water for fish containing a final concentration of 4.5 µM TNBS. The method was the same as above. The results showed that: compared with the normal control group (1.6), the number of neutrophils in intestinal tract of zebrafish in the model control group was 9.4, p<0.001, indicating that the model was established successfully and used in the following experiment 2.

Experiment 1: The treatment effect of M-Type SOD on colonitis

Experimental Method:

(1) Determine the Maximum Non-Lethal Concentration of M-Type SOD (MNLC)

Treatment of zebrafish with M-type SOD (treatment for 48 hours), set a number of different concentrations of M-type SOD;

The initial detection concentrations of M-type SOD were 150 μg/mL, 200 μg/mL, 333 μg/mL, 1000 μg/mL and 2000 μg/mL, respectively;

30 zebrafishes were treated in each experiment group;

During the experiment course, count dead zebrafish every day and remove dead zebrafish;

After the end of M-type SOD treatment, the number of dead zebrafish in each experiment group was counted and MNLC was determined.

Experimental Results:

According to the concentration-lethal data in table 1, the MNLC of M-type SOD was 150 μg/mL, and the concentration of 15 μg/mL, 50 μg/mL and 150 μg/mL were selected in pharmacodynamics evaluation experiment.

TABLE 1

M-type SOD concentration-lethal data sheet.

| Concentration (μg/mL) | Death (tail) | Death rate (%) |
|---|---|---|
| 150 | 0 | 0 |
| 200 | 6 | 20 |
| 330 | 30 | 100 |
| 1000 | 30 | 100 |
| 3000 | 30 | 100 |

(2) Evaluation of the Therapeutic Efficiency of M-Type SOD on Colonitis.

Model control group: TNBS-induced colonitis zebrafish model (model 1);

Positive control group: prednisone was added to water for fish at a final concentration of 15 μg/mL.

Treatment group: M-type SOD was added to the water for fish and the final concentrations were 1MNLC, 1/3MNLC and 1/10MNLC, respectively.

The normal control group and the solvent group were the same in the context, specifically were the wild type AB zebrafishes of 3 days after fertilization without any treatment;

Note: 30 zebrafishes were treated in each experiment group (treatment time of 48 hours); after the end of M-type SOD treatment, 15 zebrafishes were randomly observed under microscope, and pictures were taken and saved. Image analysis was performed by image analysis software, the area of zebrafish intestinal lumen was calculated, and quantitative analysis was carried out, and the statistical result was expressed with $\bar{X} \pm SE$:

The treatment of M-type SOD on colonitis was calculated as follows:

$$\text{Therapeutic efficiency (\%)} = \left(1 - \frac{\text{treatment group} - \text{solvent group}}{\text{model group} - \text{solvent group}}\right) * 100\%$$

The therapeutic efficiency of the positive control group was calculated by replacing the treatment group in the above formula with the positive control group;

Statistical analysis was performed by variance analysis and Dunnett's T-test, p<0.05 indicats a significant difference;

A representative experimental chart was provided.

Experimental Results:

Compared with the normal control group (130711), the intestinal lumen area of the model control group was 197660, p<0.001, indicating that the model was established successfully; compared with the model control group with p<0.001, the intestinal lumen area of the positive control prednisone group was 147876, the therapeutic efficiency for zebrafish colonitis is 74%. The therapeutic efficiency of M-type SOD with concentrations at 15 μg/mL, 50 μg/mL and 150 μg/mL were 66%, 82% and 84% respectively, each group compared with the model control group with p<0.001, indicating the significant therapeutic efficiency of M-type SOD on colonitis. Please refer to table 2, FIGS. 5, 6, 7 and 8 for details.

TABLE 2

The quantitative results of the therapeutic efficiency of M-type SOD on colonitis (n = 15).

| group | Concentration (μg/mL) | intestinal lumen area (mean ± SE) | therapeutic efficiency (%) |
|---|---|---|---|
| normal control group | — | 130711 ± 7075 | — |
| model control group | — | 197660 ± 6280 | — |
| prednisone | 15 | 147876 ± 5809*** | 74%*** |
| M-type SOD | 15 | 153560 ± 6080*** | 66%*** |
| | 50 | 142595 ± 3167*** | 82%*** |
| | 150 | 141259 ± 5359*** | 84%*** |

Compared with the model control group,
***p < 0.001

Experiment 2: Effects of M-Type SOD on inflammation resolution of colonitis

Experimental Method:

Tests were carried out at 3 concentrations of M-type SOD (added to the water for fish with final concentrations of 15 μg/mL, 50 μg/mL and 150 μg/mL);

Model control group: TNBS-induced colonitis zebrafish model (model 2);

Treatment group: M-type SOD was added to treat the colonitis zebrafish model;

Positive control group: prednisone was added to water for fish at a final concentration of 15 μg/mL;

The normal control group and the solvent group are the same in the context, specifically refer to the untreated transgenic neutrophil fluorescent zebrafish;

30 transgenic neutrophil fluorescent zebrafishes were treated in each experiment group for 48 hours;

After the end of M-type SOD treatment, 12 zebrafishes were randomly observed under fluorescent microscope, and pictures were taken and saved;

The distribution of neutrophils in colonitis tissue was quantitatively analyzed by image analysis software; the result of statistical analysis was showed as $\bar{X} \pm SE$, the pharmacokinetic calculation formula of M-type SOD on colonitis inflammation resolution was as follows:

$$\text{Therapeutic efficiency (\%)} = \left(1 - \frac{\text{treatment group} - \text{solvent group}}{\text{model group} - \text{solvent group}}\right) * 100\%$$

The therapeutic efficiency of the positive control group was calculated by replacing the treatment group in the above formula with the positive control group;

Statistical analysis was performed by variance analysis and Dunnett's T-test, $p<0.05$ indicating a significant difference;

A representative experimental chart was provided.

Experimental Results

Figure 9:
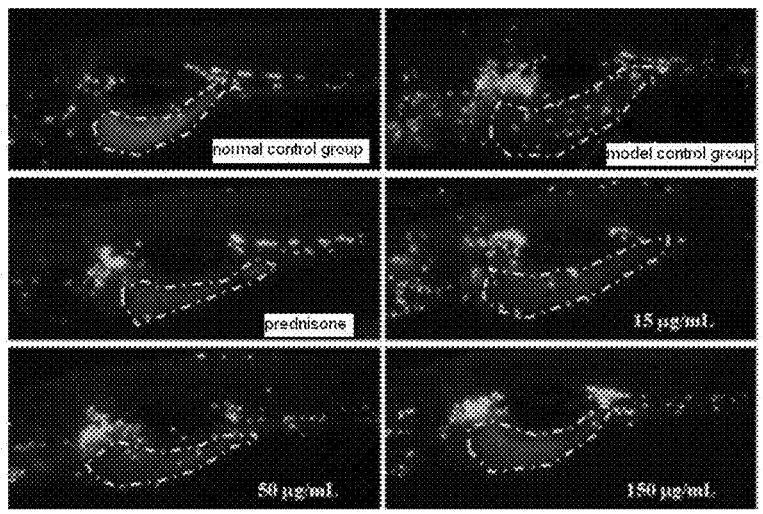
FIG. 9 is a phenotype chart showing the improvement of the mutant high temperature resistant SOD on colonitis inflammation resolution.
Figure 10:
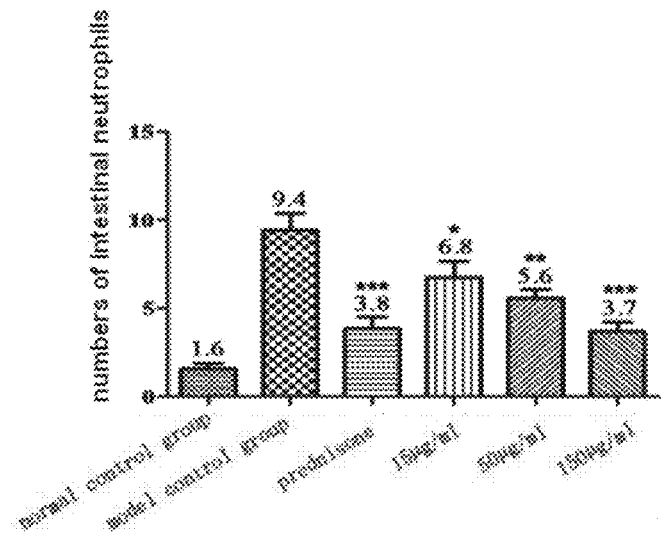
FIG. 10 is a comparison chart showing the treatment efficacy of the mutant high temperature resistant SOD on colonitis inflammation resolution (numbers of neutrophils)
Figure 11:
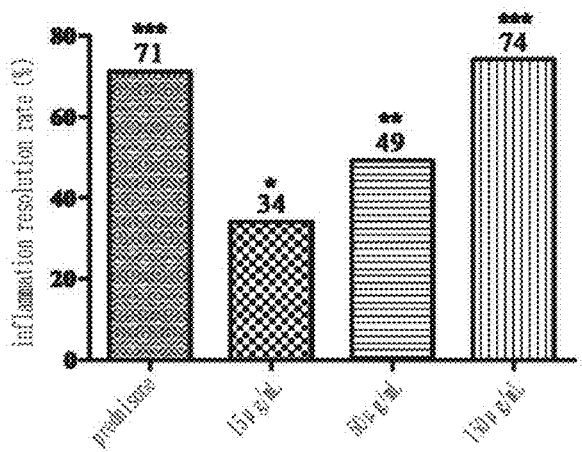
FIG. 11 is a comparison chart showing the improvement rate of the mutant high temperature resistant SOD on colonitis inflammation resolution.

Compared with the normal control group (1.6), the number of neutrophils in the intestinal tract of zebrafish in model control group was 9.4, $p<0.001$, indicating that the model was established successfully. Compared with the model control group, the number of neutrophils in positive control prednisone group was 3.8, $p<0.001$, indicating that prednisone has the effect of promoting the inflammation resolution of colitis with an inflammation resolution rate of 71%. The therapeutic efficiency of M-type SOD at 15 μg/mL, 50 μg/mL and 150 μg/mL on the inflammation resolution of colitis were 34%, 49% and 74% respectively, with $p<0.05$ & $p<0.01$ & $p<0.001$ of each group, compared with the model control group, indicating that M-type SOD has a significant effect on inflammation resolution of colitis. See Table 3, FIG. 9, FIG. 10 and FIG. 11 for details.

TABLE 3

The quantitative results of the promoting effect of M-type SOD on colitis inflammation resolution (n = 12).

| group | Concentration (μg/mL) | number of neutrophils (mean ± SE) | inflammation resolution rate (%) |
|---|---|---|---|
| normal control group | — | 1.6 ± 0.30 | — |
| model control group | — | 9.4 ± 0.94 | — |
| prednisone | 15 | 3.8 ± 0.64*** | 71%*** |
| M-type SOD | 15 | 6.8 ± 0.88* | 34%* |
|  | 50 | 5.6 ± 0.45** | 49%** |
|  | 150 | 3.7 ± 0.53*** | 74%*** |

Compared with the model control group,
*p < 0.05
**p < 0.01
***p < 0.001.

Experiment 3: Pathological analysis of intestinal tract tissue

Groups: Experiment group 1, normal control group; experiment group 2, model control group; experiment group 3, positive control drug prednisone 15 μg/mL; experiment group 4, M-type SOD15 μg/mL; experiment group 5, M-type SOD 50 μg/mL; experiment group 6, M-type SOD 150 μg/mL.

Experimental Method:

M-type SOD treatment group: treatment mode, concentrations were the same as in experiment 1;

Positive control group: prednisone treatment group (the same as above);

Enteritis model group: model 1;

Normal control group: wild type AB zebrafish of 3 days after fertilization without any treatment;

30 zebrafishes were treated in each experiment group for 48 hours;

After treatment with M-type SOD, the mixture was fixed with 4% paraformaldehyde and then the zebrafish was transferred to 70% ethanol;

The fixed zebrafish was observed under the microscope for the colonic tissue and photographed for histopathological analysis, as described in the experimental results.

Experimental Results

Figure 12:
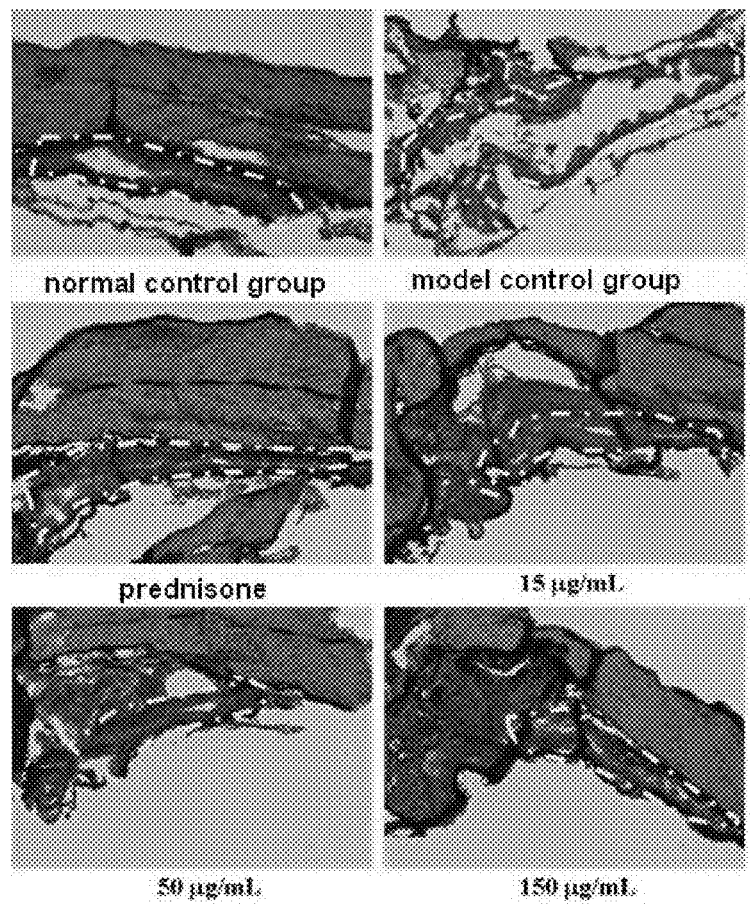
FIG. 12 is a chart showing the histopathological analysis of the therapeutic efficiency of the mutant high temperature resistant SOD on colonitis.

In the normal control group, the intestinal mucosa of the zebrafish was smooth and intact, and the intestinal folds were obvious. In the model control group, the zebrafish had a expansion of intestinal lumen, the intestinal mucosa became thinner and the intestinal folds disappeared, and the mucosal erosion and ulcer was observed. After the treatment with the positive control drug prednisone, intestinal mucosal histology was improved significantly. After treatment with M-type SOD at concentrations of 15 μg/mL, 50 μg/mL and 150 μg/mL, the intestinal lumen area and intestinal folds were restored substantially, the inflammation of intestinal mucosa was significantly improved, and no obvious inflammatory ulcer was observed. See FIG. 12 for details.

Example 4: Therapeutic Efficiency of M-Type SOD Provided by the Present Invention on Human Enteritis (Clinical Observation)

Inflammatory bowel disease (IBD) is a common disease, Crohn's disease (CD) and ulcerative colitis (UC) are often known as IBD. Crohn's disease is also known as regional enteritis, segmental enteritis or granulomatous enterocolitis. The disease is a gastrointestinal chronic granulomatous disease with unknown causes, more common in the terminal ileum and near the colon, the lesions are of a phased or leaping distribution, which is a whole layer of intestinal inflammation. Ulcerative colitis, also known as non-specific ulcerative colitis, is a rectum and colon chronic inflammatory disease with unknown causes. Lesions mainly involve the large intestine mucosa and submucosa, rectum and distal colon is the most common parts of being affected, but the whole colon and terminal ileum can also be involved when the lesions are severe. Their symptoms are generally diarrhea, abdominal pain, and even some people can have bloody stools. It is thought that the pathogenesis of IBD may be: certain genetic determinants render susceptible individuals susceptible to disease, stimulate mucosa-associated lymphoid tissue under the action of infectious agents or intestinal antigens, causing up-regulation of T-cell responses, thereby activating various cytokine network, leading to local tissue inflammation, and then continue to enlarge and sustain, causing intestinal damage and the corresponding clinical manifestations. Treatment often uses glucocorticosteroids (GCS) drugs (prednisone, adrenal cortex hormones) and antibiotics. Such treatment often has a poor efficacy, severe side effects, and drug resistance can be easily developed. We have attempted to verify the therapeutic efficiency of the present invention in the form of tablets (each containing M-type SOD 10000 U) in the present invention, and the tablets were prepared as follows.

M-type SOD tablets prescription: M-type SOD 2 g; lactose 40 g; pregelatinized starch 50 g; povidone K30 6 g; magnesium stearate 1 g.

Preparation Process:

1、 M-type SOD powder is passed over 80 mesh sieve for use;

2、 Adhesive preparation: weigh and add prescription dosage of povidone k30 to appropriate amount of 75% ethanol (about 60 g), stirred for use;

3. Prescription amount of pregelatinized starch, lactose, prescription amount of SOD were weighed and mixed evenly;

4. Granulation: the adhesive obtained in step 2 was added to the above-mentioned mixed powder and made into soft material, and then granulated with a 20 mesh sieve;

5. Wet granules were dried at 60±2° C. to a water content of 1.0% to 3.5%, granulated with a 20 mesh sieve;

6. Mix the prescription amount of magnesium stearate with dry granules evenly;

7. Tablet compressing machine was used for tabletting, each tablet contains 10,000 units of M-type SOD.

In this example, 63 volunteers were tested for this product, including 37 males and 26 females, of whom 21 cases of 30-40 years old, 30 cases of 40 to 50 years old, 12 cases over 50 years old.

Diagnostic criteria: Because of the lack of specific diagnostic criteria for UC, and CD is difficult to obtain histopathological results so as to confirm the diagnosis, i.e. non-caseous granuloma, it is still difficult to diagnose the etiology and disease type of IBD currently. However, IBD patients have common clinical manifestations of perennial repeated abdominal pain and diarrhea, and one can observe and record whether these symptoms are improved and eased.

Application method: one tablet per night, taking 10 consecutive days for a treatment course.

Efficacy Evaluation Criteria:

Excellent: the use of 10 days without diarrhea and abdominal pain phenomenon, having a formed stool.

Improved: occasionally with diarrhea and abdominal pain phenomenon.

Invalid: Diarrhea and abdominal pain was not improved.

Result:

Experimental Drug:

The M-type SOD prepared in Example 1, white powder, was prepared at a concentration of 20 mg/mL with ultrapure water at the time of application as mother solution, fresh made.

Indometacin, white powder, batch number 1108939, was prepared at a concentration of 60 mM with 100% DMSO at the time of application as mother solution, provided by the Shanghai Crystal Pure Industrial Co., Ltd.

Lipopolysaccharide (LPS), white powder, batch number L-2880, was prepared at a concentration of 10 mg/mL with 100% DMSO at the time of application as mother solution, provided by Sigma of the United States.

Dimethyl sulfoxide (DMSO), Sigma, batch number BCBN0845V.

Copper sulfate pentahydrate, Xilong Chemical Co. Ltd., batch number 120201.

Instruments and Reagents Used:

Dissection microscope (SZX7, OLYMPUS, Japan); motorized zoom fluorescence microscopy which can continuously switch magnifications (AZ100, Nikon Corporation, Japan); 6-well plates (Nest Biotech, China); methylcellulose (Aladdin, Shanghai, Chi na).

The Maximum Non-Lethal Concentration of M-Type SOD (MNLC)

Treat zebrafish with M-type SOD for 5 hours, and the six detection concentrations of M-type SOD were 15 μg/mL, 50 μg/mL, 150 μg/mL, 450 μg/mL, 1350 μg/mL and 2000 μg/mL respectively. 30 zebrafishes were treated in each experiment group. During the course of the experiment, the dead zebrafishes were counted and removed. After the M-type SOD treatment, the number of dead zebrafishes in each experiment group was counted, and MNLC was deter-

| Disease type | Number of application | Treatment time | Excellent Cases | Excellent % | Improved Cases | Improved % | Invalid Cases | Invalid % | Total efficacy % |
|---|---|---|---|---|---|---|---|---|---|
| IBD | 63 | 10 Days | 44 | 69.8% | 16 | 25.4% | 3 | 4.8% | 95.2% |

The above-described Example 3-4, from the animal models and the clinical observation of the patients respectively, demonstrated that the M-type SOD of the present invention had a significant therapeutic efficiency on various inflammatory bowel diseases, and the therapeutic efficiency of M-type SOD of the present invention is superior to that of the hormone prednisone.

Example 5: The Research on the M-Type SOD Provided by the Present Invention for Anti-Inflammation Caused by Exogenous Inflammatory Factors Experimental Animals Transgenic neutrophil fluorescent zebrafish (provided by Hunter Biotechnology, Inc) are in a natural pair of mating breeding mode. A total of 810, with each experiment group of 30, the age of 3 days after fertilization are used. The zebrefishes were kept in water for fish at 28° C. (Water quality: adding 200 mg instant sea salt per liter reverse osmosis water, conductivity of 480~510 μS/cm, pH: 6.9~7.2; hardness of 53.7~71.6 mg/L $CaCO_3$), experimental animal use license number: SYXK (Zhejiang) 2012-0171. Feed management is in line with international AAALAC certification requirements.

mined. The results showed that M-type SOD at 2000 μg/mL concentration for 5 hours still had no toxic effects on zebrafish. Therefore, the concentration of 2000 μg/mL was selected as the maximum concentration in the evaluation of anti-inflammatory effect of SOD.

Experiment 1: Evaluation of the anti-inflammatory effect of M-Type SOD on copper sulfate-induced inflammation Groups: Experiment group 1, normal control group, specifically refers to untreated transgenic neutrophil fluorescent zebrafish; experiment group 2, model control group; experiment group 3, positive control drug indometacin 60 μM; experiment group 4, M-type SOD15 μg/mL; experiment group 5, M-type SOD 50 μg/mL; experiment group 6, M-type SOD150 μg/mL; experiment group 7, M-type SOD 450 μg/mL; experiment group 8, M-type SOD 1350 μg/mL; experiment group 9, M-type SOD 2000 μg/mL.

Concentration Determining Basis:

According to the above exploratory test of concentration, SOD at concentration of 2000 μg/mL had no toxic effect on zebrafish, so 2000 μg/mL was selected as the maximum concentration of SOD for anti-inflammatory effect. The anti-inflammatory concentrations were set at 15 μg/mL, 50 μg/mL, 150 μg/mL, 450 μg/mL, 1350 μg/mL and 2000 μg/mL.

Model Making

The zebrafish inflammation model was established by treatment of transgenic neutrophil fluorescent zebrafish with 10 µM of copper sulfate pentahydrate dissolved in water. The specific method was described by d'Alencon et al., BMCBiology. 2010, 8: 151, A high-throughput chemically induced inflammation assay in zebrafish. Compared with the number of neutrophils at the inflammatory site (the region of auditory cells) in the normal control group (1.3), the number in the model control group was 15.5, p<0.001, indicating that the model was established successfully.

Experimental Method

The transgenic neutrophil fluorescent zebrafish were randomly selected and put in the six-well plate, each well 30, using copper sulfate induced zebrafish inflammation model. Water-soluble M-type SOD15 µg/mL, 50 µg/mL, 150 µg/mL, 450 µg/mL, 1350 µg/mL and 2000 µg/mL; the positive control drug indometacin concentration was 60 µM; 3 mL per well of the drug solution was added, and the normal control group and the model control group were set up at the same time. The treatment time of M-type SOD was 5 hours, 10 zebrafishes were randomly selected to be observed under the fluorescence microscope, and images were taken and saved. The images were analyzed by Nikon NIS-ElementsD3.10 advanced image processing software. The number of neutrophils (N) in zebrafish was calculated and quantitatively analyzed. The calculation formula of the rate of inflammation resolution was as follows:

$$\text{Inflammation resolution (\%)} = \left[\frac{N(\text{Model ctrl group}) - N(\text{subject group})}{N(\text{Model ctrl group})}\right] * 100\%.$$

The subject group included the M-type SOD treatment group and the positive control indometacin treatment group.

Statistical analysis used variance analysis and Dunnett's T-test, p<0.05 indicating of significant differences; providing a representative experimental chart.

Experimental Results

Figure 13:
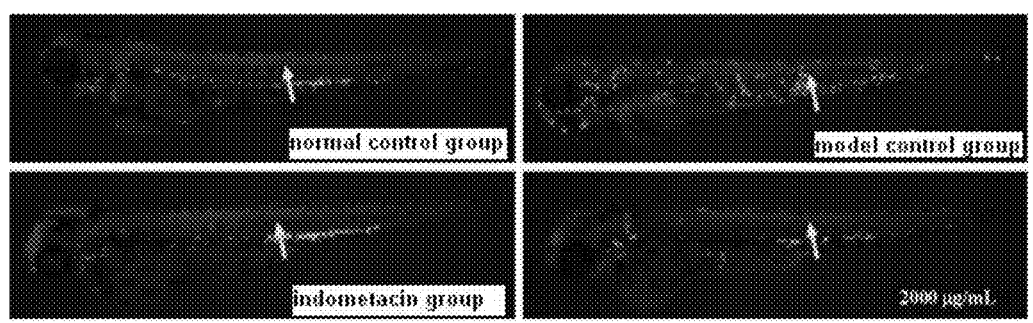
FIG. 13 is a phenotype chart showing the anti-inflammatory effect of the mutant high temperature resistant SOD against inflammation of zebrafish (Note: arrows refer to neutrophils on inflammatory site)
Figure 14:
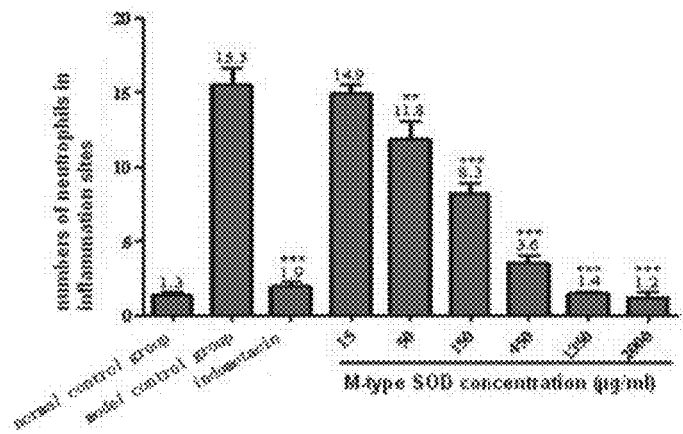
FIG. 14 is a comparison chart showing the anti-inflammatory effect (numbers of neutrophils) of the mutant high temperature resistant SOD on inflammation of zebrafish (compared to the model control group, $p<0.01$, *$p<0.001$)
Figure 15:
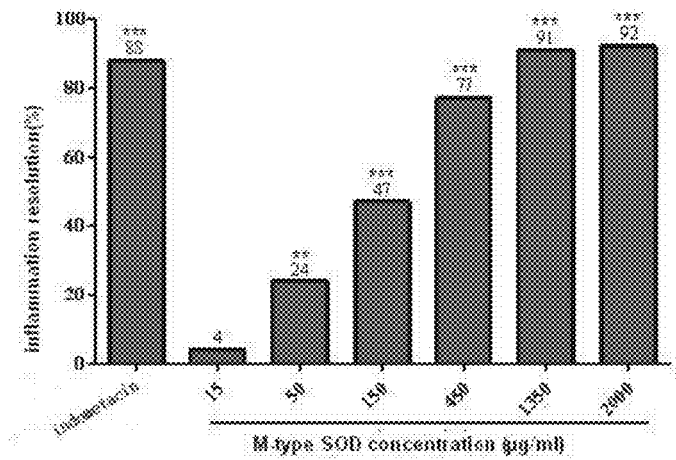
FIG. 15 is a comparison chart showing the inflammation resolution rate of the mutant high temperature resistant SOD on inflammation of zebrafish (compared to the model control group, $p<0.01$, *$p<0.001$)

Compared with the normal control group (1.3), the number of neutrophils at the inflammatory site in the model control group was 15.5, p<0.001, indicating that the model was established successfully; compared with the model control group, the number of neutrophils at the inflammatory site in the indometacin group was 1.9, p<0.001, indicating that indometacin had anti-inflammatory effect. The numbers of neutrophils at the inflammatory site were 14.9, 11.8, 8.3, 3.6, 1.4 and 1.2 respectively at the M-type SOD concentrations of 15 µg/mL, 50 µg/mL, 150 µg/mL, 450 µg/mL, 1350 µg/mL and 2000 µg/mL groups, the rates of inflammation resolution were 4%, 24%, 47%, 77%, 91% and 92%, respectively. Compared with the model control group, the remaining groups were p<0.05 & p<0.01 & p<0.001, indicating that M-type SOD at the experimental concentrations had a significant anti-inflammatory effect on copper sulfate-induced zebrafish inflammation, except the 15 µg/mL and 50 µg/mL groups, and showed a dose-dependent manner. See Table 4, FIG. 13, FIG. 14 and FIG. 15 for details.

TABLE 4

Quantitative results of anti-inflammatory effects of M-type SOD on zebrafish inflammation (n = 12).

| group | Concentration | numbers of neutrophils (mean ± SE) | Inflammation resolution rate (%) |
|---|---|---|---|
| normal control group | — | 1.3 ± 0.2 | — |
| model control group | — | 15.5 ± 1.1 | — |
| indometacin | 60 µM | 1.9 ± 0.3*** | 88*** |
| M-type SOD | 15 µg/mL | 14.9 ± 0.6 | 4 |
|  | 50 µg/mL | 11.8 ± 1.2** | 24** |
|  | 150 µg/mL | 8.3 ± 0.6*** | 47*** |
|  | 450 µg/mL | 3.6 ± 0.5*** | 77*** |
|  | 1350 µg/mL | 1.4 ± 0.2*** | 91*** |
|  | 2000 µg/mL | 1.2 ± 0.4*** | 92*** |

Compared with the model control group,
**p < 0.01,
***p < 0.001.

Experiment 2: Evaluation of anti-inflammatory effect of M-type SOD on LPS-induced inflammation.

Concentration group: Experiment group 1, normal control group, specifically refers to untreated transgenic neutrophil fluorescent zebrafish; experiment group 2, model control group; experiment group 3, positive control drug indometacin 60 µM; experiment group 4, M-type SOD15 µg/mL; experiment group 5, M-type SOD 50 µg/mL; experiment group 6, M-type SOD150 µg/mL, experiment group 7, M-type SOD 450 µg/mL; experiment group 8, M-type SOD 1350 µg/mL; experiment group 9, M-type SOD 2000 µg/mL.

Model Making

The zebrafish inflammation model was established by treatment of transgenic neutrophil fluorescent zebrafish through LPS injection. Compared with the normal control group (2.4), in the model control group, the number of neutrophils at the inflammatory site (yolk sac area) was 17.8, p<0.001, indicating that the model was established successfully. (See Li-LingYang et al., Molecules, 2014, 19, 2390-2409. Endotoxin Molecule Lipopolysaccharide-Induced Zebrafish Inflammation Model: A Novel Screening Method for Anti-Inflammatory Drugs.)

Experimental Method

The zebrafishes were randomly selected and put in the six-well plate, 30 per well. The LPS-induced zebrafish inflammation model was given water-soluble M-type SOD 15 µg/mL, 50 µg/mL, 150 µg/mL, 450 µg/mL, 1350 µg/mL and 2000 µg/mL respectively; the concentration of positive control drug indometacin was 60 µM, 3 mL drug liquid per well was added. The normal control group and model control group were set at the same time. After 5 hours treatment, 10 zebrafishes were randomly selected from each group to be observed under fluorescence microscopy, images were taken and saved. Image analysis was performed with Nikon NIS-Elements D3.10 advanced image processing software, the number of neutrophils (N) in zebrafish was calculated, and quantitatively analyzed. The formula of the rate of inflammation resolution was as follows:

$$\text{Inflammation resolution (\%)} = \left[\frac{N(\text{Model ctrl group}) - N(\text{subject group})}{N(\text{Model ctrl group})}\right] * 100\%,$$

The subjects group included the M-type SOD treatment group and the positive control indometacin treatment group.

Statistical analysis used variance analysis and Dunnett's T-test, p<0.05, indicating of significant differences; providing a representative experimental chart.

Experimental Results

Figure 16:
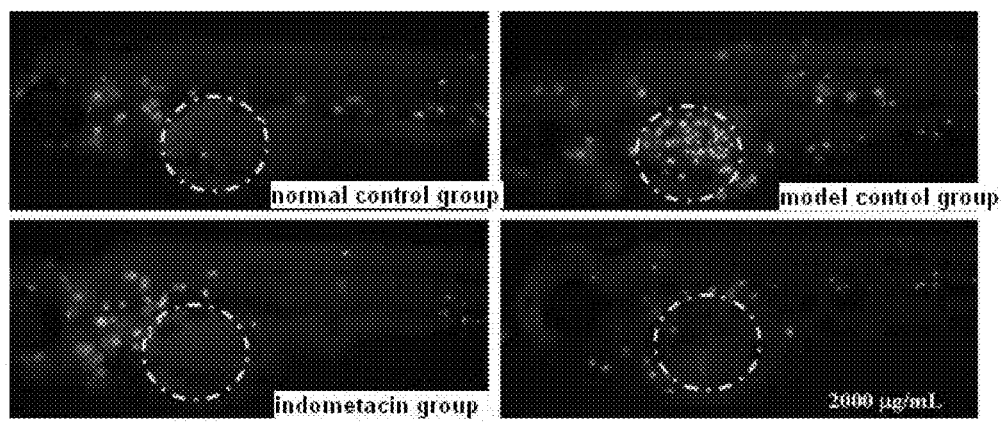
FIG. 16 is a phenotype chart showing the anti-inflammatory effect of the mutant high temperature resistant SOD against inflammation of zebrafish (Note: the framed region is the neutrophils on inflammatory site)
Figure 17:
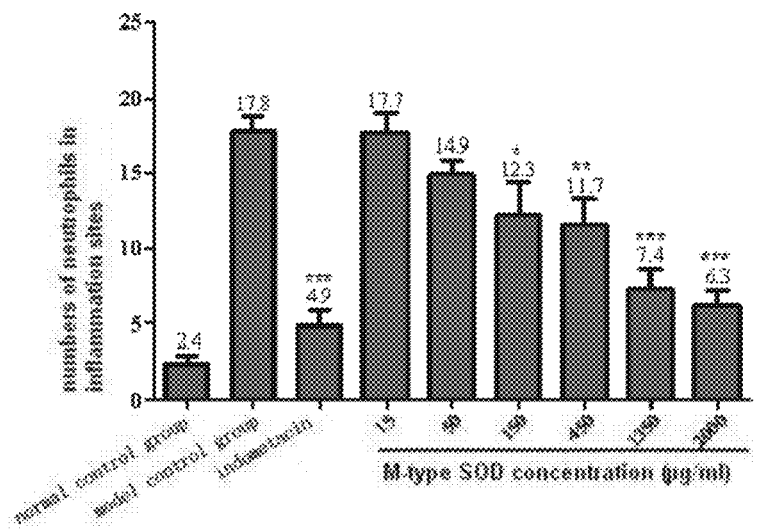
FIG. 17 is a comparison chart showing the anti-inflammatory effect (numbers of neutrophils) of the mutant high temperature resistant SOD on inflammation of zebrafish (compared to the model control group, *$p<0.05$, $p<0.01$, *$p<0.001$)
Figure 18:
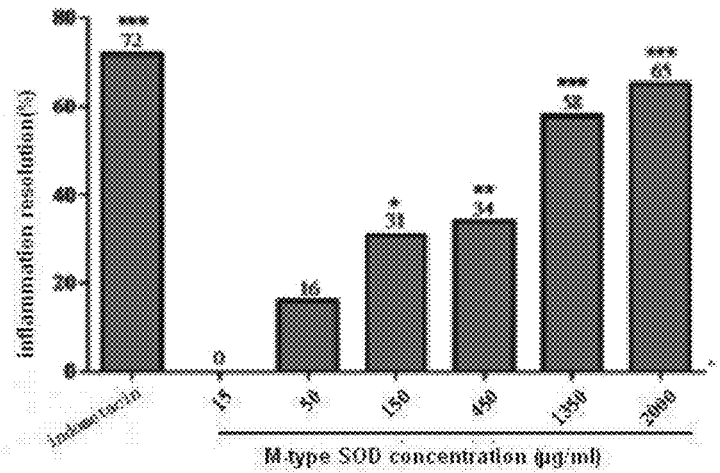
FIG. 18 is a comparison chart showing the inflammation resolution rate of the mutant high temperature resistant SOD on inflammation of zebrafish (compared to the model control group, *$p<0.05$, $p<0.01$, *$p<0.001$)

Compared with the normal control group (2.4), the number of neutrophils in the model control group was 17.8, p<0.001, indicating that the model was established successfully. Compared with the model control group, he number of neutrophils at the inflammatory site in the indometacin group was 4.9, p<0.001, the rate of inflammatory resolution was 72%, indicating that indometacin had an anti-inflammatory effect. The number of neutrophils at the inflammatory sites were 17.7, 14.9, 12.3, 11.7, 7.4 and 6.3, respectively, at the M-type SOD concentrations of 15 μg/mL, 50 μg/mL, 150 μg/mL, 450 μg/mL, 1350 μg/mL and 2000 μg/mL groups, the rates of inflammation resolution were 0%, 16%, 31%, 34%, 58% and 65%, respectively. Compared with the model control group, the remaining groups were p<0.05 & p<0.01 & p<0.001 except the 15 μg/mL and 50 μg/mL groups, indicating that M-type SOD at the experimental concentrations had a significant anti-inflammatory effect on LPS-induced zebrafish inflammation, and showed a dose-dependent manner. See Table 5, FIG. 16, FIG. 17 and FIG. 18 for details.

TABLE 5

Quantitative results of anti-inflammatory effects of M-type SOD on zebrafish inflammation (n = 12).

| group | Concentration | numbers of neutrophils (mean ± SE) | Inflammation resolution rate (%) |
|---|---|---|---|
| normal control group | — | 2.4 ± 0.5 | — |
| model control group | — | 17.8 ± 1.0 | — |
| indometacin | 60 μM | 4.9 ± 1.0*** | 72*** |
| M-type SOD | 15 μg/mL | 17.7 ± 1.4 | 0 |
|  | 50 μg/mL | 14.9 ± 1.0 | 16 |
|  | 150 μg/mL | 12.3 ± 2.1* | 31* |
|  | 450 μg/mL | 11.7 ± 1.6** | 34** |
|  | 1350 μg/mL | 7.4 ± 1.3*** | 58*** |
|  | 2000 μg/mL | 6.3 ± 1.0*** | 65*** |

Compared with the model control group,
*p < 0.05,
**p < 0.01,
***p < 0.001

Experiment 3: Evaluation of anti-inflammatory effect of M-type SOD on inflammation of tail amputation injury.

Groups: Experiment group 1, normal control group, specifically refers to untreated transgenic neutrophil fluorescent zebrafish; experiment group 2, model control group; experiment group 3, positive control drug indometacin 60 μM; experiment group 4, M-type SOD 150 μg/mL, experiment group 5, M-type SOD 450 μg/mL; experiment group 6, M-type SOD 1350 μg/mL; experiment group 7, M-type SOD 2000 μg/mL.

Model making: The model of zebrafish inflammation was established by mechanical amputation of tail fins of transgenic neutrophil fluorescent zebrafish. Compared with the normal control group (4.8), the number of neutrophils at the inflammatory site was 20.2 in the model control group, p<0.001, indicating that the model was established successfully. The most famous zebrafish damage model is the fish larvae tail trauma model, in which a part of tail fins of the larvae were amputated. The researchers used the transgenic zebrafish damage model to study the latest mechanism of neutrophil chemotaxis to the site of injury by green fluorescent protein (EGFP) expressed under the transcription control of neutrophil-specific peroxidase catalyst. (Specifically see J. Yuan, S. Shaham, S. Ledoux, et al. The *C. elegans* cell death gene ced-3 encodes a protein similar to mammalian interleukin-1β-converting enzyme [J]. Cell, 1993, 641-652.)

Experimental Method

The transgenic neutrophil fluorescent zebrafish were randomly selected and put in the six-well plate after mechanical amputation of tail fins, 30 per well. Each group was given water-soluble M-type SOD 150 μg/mL, 450 μg/mL, 1350 μg/mL, and 2000 μg/mL respectively; the concentration of positive control drug indometacin was 60 μM, 3 mL drug solution per well. The normal control group and model control group were set at the same time. After 5 hours treatment, 10 zebrafishes from each group was randomly selected and observed under fluorescence microscopy, the pictures were taken and saved. Image analysis was performed with Nikon NIS-Elements D3.10 advanced image processing software, the number of neutrophils (N) in zebrafish was calculated, and quantitatively analyzed. The formula of the rate of inflammation resolution was as follows:

$$\text{Inflammation resolution (\%)} = \left[\frac{N(\text{Model ctrl group}) - N(\text{subject group})}{N(\text{Model ctrl group})}\right] * 100\%,$$

The subject group included the M-type SOD treatment group and the positive control indometacin treatment group.

Statistical analysis used variance analysis and Dunnett's T-test, p<0.05, indicating of significant differences; providing a representative experimental chart.

Experimental Results

Figure 19:
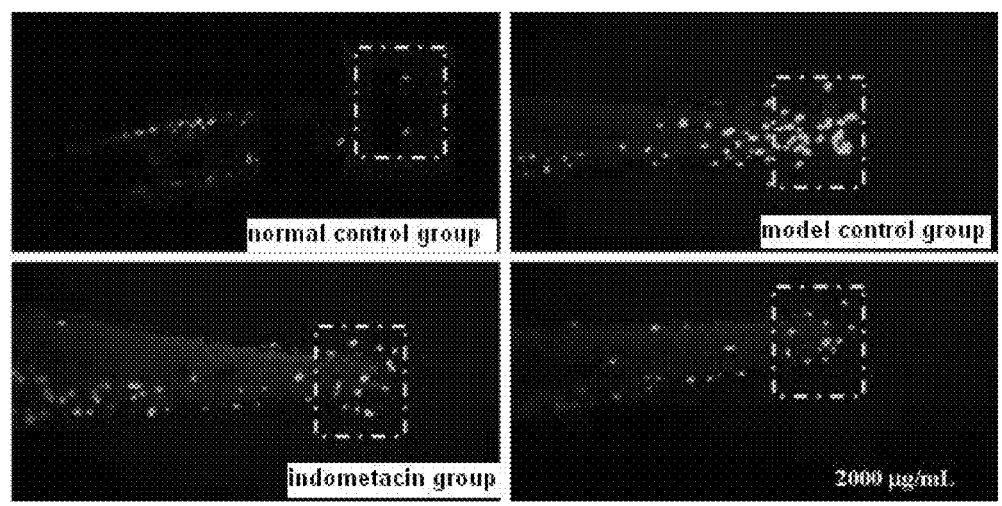
FIG. 19 is a phenotype chart showing the anti-inflammatory effect of the mutant high temperature resistant SOD against inflammation of zebrafish (Note: the framed region is the neutrophils on inflammatory site)
Figure 20:
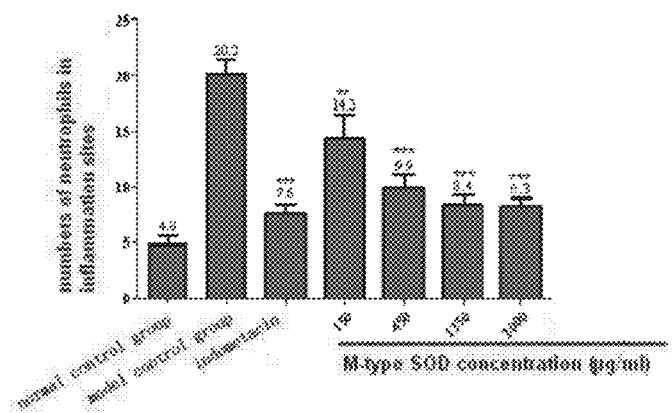
FIG. 20 is a comparison chart showing the anti-inflammatory effect (numbers of neutrophils) of the mutant high temperature resistant SOD on inflammation of zebrafish (compared to the model control group, $p<0.01$, *$p<0.001$)
Figure 21:
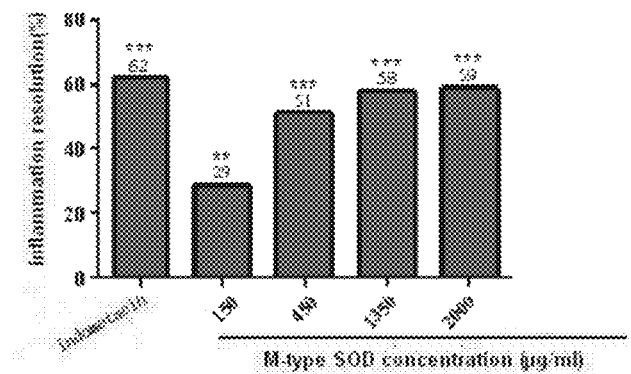
FIG. 21 is a comparison chart showing the inflammation resolution rate of the mutant high temperature resistant SOD on inflammation of zebrafish (compared to the model control group, $p<0.01$, *$p<0.001$)

Compared with the normal control group (4.8), the number of neutrophils at the inflammatory site in the model control group was 20.2, p<0.001, indicating that the model was established successfully. Compared with the model control group, the number of neutrophils at the inflammatory site in the indometacin group was 7.6, p<0.001, the rate of inflammatory resolution was 62%, indicating that indometacin had an anti-inflammatory effect. The number of neutrophils at the inflammatory sites were 14.3, 9.9, 8.4 and 8.3, respectively, at the M-type SOD concentrations of 150 μg/mL, 450 μg/mL, 1350 μg/mL and 2000 μg/mL groups. The rates of inflammation resolution were 29%, 51%, 58% and 59%, respectively, compared with the model control group, the groups were p<0.01 & p<0.001, indicating that M-type SOD at the above experimental concentrations had a significant anti-inflammatory effect on tail amputation injury zebrafish inflammation, and showed a dose-dependent manner. See Table 6, FIG. 19, FIG. 20 and FIG. 21 for details.

TABLE 6

Quantitative results of anti-inflammatory effects of M-type SOD on zebrafish inflammation (n = 12).

| group | Concentration | numbers of neutrophils (mean ± SE) | Inflammation resolution rate (%) |
|---|---|---|---|
| normal control group | — | 4.8 ± 0.7 | — |
| model control group | — | 20.2 ± 1.2 | — |
| indometacin | 60 µM | 7.6 ± 0.9*** | 62*** |
| | 150 µg/mL | 14.3 ± 2.1** | 29** |
| | 450 µg/mL | 9.9 ± 1.2*** | 51*** |
| M-type SOD | 1350 µg/mL | 8.4 ± 0.8*** | 58*** |
| | 2000 µg/mL | 8.3 ± 0.6*** | 59*** |

Compared with the model control group,
**$p < 0.01$,
***$p < 0.001$.

The above experiments 1-3 showed that the M-type SOD of the present invention had a significant anti-inflammatory effect on a variety of exogenous stimuli such as copper sulfate, LPS and tail amputation-induced zebrafish inflammation. In the above experiments, LPS, by continuously stimulating the mononuclear macrophage system, produces a large number of bioactive substances such as cytokines, reactive oxygen etc, causing cell damage and apoptosis, eventually leading to uncontrolled inflammatory response; $CuSO_4$ can damage the zebrafish auditory cells to cause inflammation, which was used to study the local inflammatory response; tail-injury test used mechanics to amputate the zebrafish tail fins, which is used to study the inflammatory response caused by damage. Whether the model had been established successfully was determined by microscopic observation of the number of neutrophils of transgenic neutrophil fluorescent zebrafish, and then treated with drugs (indometacin) and M-type SOD. Indometacin is non-steroidal anti-inflammatory drug, with anti-inflammatory, antipyretic and analgesic effects. But the incidence of adverse reactions of indometacin is relatively high. After drug treatment, the number of neutrophils at the inflammatory site was reduced, indicating that the faster the inflammation resolution was, the better anti-inflammatory effects the drug had. The above experimental data showed that: no matter whether the inflammation was systemic, local or mechanical injury, the treatment effect of M-type SOD was superior or equal to the drug indometacin.

Example 6. The Therapeutic Effect of the Mutant High Temperature Resistant Superoxide Dismutase (M-Type SOD) of the Present Invention on Skin Inflammation Experiment 1: The clinical observation of the present invention in the treatment of dermatitis eczema.

A total of 51 volunteers were administrated with this product (M-type SOD dissolved in glycerol, mixed homogeneously, with a final concentration of 4000-6000 U/mg), including 24 males and 27 females, of which 14 cases were 5 to 15 years old, 26 cases were 20-30 years old, 6 cases were 40 to 50 years old, 5 cases were over 50 years old.

Figure 22:
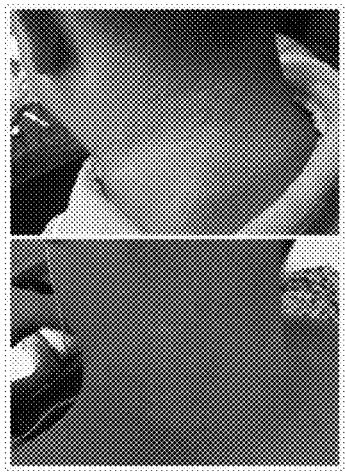
FIG. 22 is a comparison chart showing the effect of the mutant high temperature resistant SOD according to the present invention on the treatment of dermatitis eczema.

Diagnostic criteria: dermatitis eczema manifested as: skin turns red, slightly swollen when severe, papules, blisters on top, itchy, discharging pus when scratching, scab (see FIG. 22, the upper picture).

Method of application: The product of the invention was applied to the skin surface of the patients three times a day, for 7 days as a treatment course.

Efficacy Evaluation Criteria:

Excellent: the skin returns to normal after applying for a week.

Improved: 80% of the skin returns to normal (see FIG. 22, the lower picture).

Invalid: local skin does not meet the criteria of improvement, or no improvement, or even continues to deteriorate.

Result:

| Disease type | Number of patients | Treatment time | Excellent Cases | Excellent % | Improved Cases | Improved % | Invalid Cases | Invalid % | Total efficacy % |
|---|---|---|---|---|---|---|---|---|---|
| Dermatitis eczema | 51 | 7 Days | 39 | 76.5% | 11 | 21.6% | 1 | 1.9% | 98.1% |

Experiment 2. The clinical observation of the present invention in the treatment of tinea pedis.

A total of 47 volunteers were administrated with this product (M-type SOD dissolved in glycerol, mix homogeneously, with a final concentration of 4000-6000 U/mg), including 22 males and 25 females, of which 18 cases were 15 to 30 years old, 23 cases were 30-50 years old, 6 cases were over 50 years old.

Figure 23:
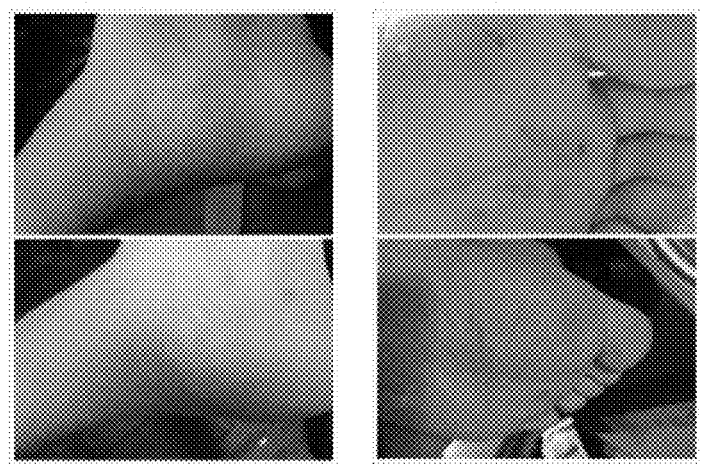
FIG. 23 is a comparison chart showing the effect of the mutant high temperature resistant SOD according to the present invention on the treatment of tinea pedis.

Diagnostic criteria: tinea manus and pedis symptom: keratosis of the skin between toes (fingers), blisters, pimples, erosion, red and swollen, often accompanied by local red and swollen, seriously itching (see FIG. 23, the upper two pictures).

Method of application: The product of the invention was applied to the skin surface of the patient three times a day, for 7 days as a treatment course.

Efficacy Evaluation Criteria:

Excellent: the skin returns to normal after applying for a week (see FIG. 23, the lower two pictures).

Improved: 80% of the skin returns to normal.

Invalid: local skin does not meet the criteria of improvement, or no improvement, or even continue to deteriorate.

Result:

| Disease type | Number of patients | Treatment time | Excellent | | Improved | | Invalid | | Total efficacy % |
|---|---|---|---|---|---|---|---|---|---|
| | | | Cases | Excellent % | Cases | Improved % | Cases | Invalid % | |
| tinea manus and pedis | 47 | 7 Days | 33 | 70.2% | 13 | 27.7% | 1 | 2.1% | 97.9% |

Experiment 3. The clinical observation of present invention in the treatment of allergic dermatitis A total of 74 volunteers tried this product (M-type SOD dissolved in glycerol, mix homogeneously, with a final concentration of 4000-6000 U/mg), including 38 males and 36 females, of which 34 cases were 15 to 30 years old, 31 cases were 30-50 years old, 9 cases were over 50 years old.

Figure 24:
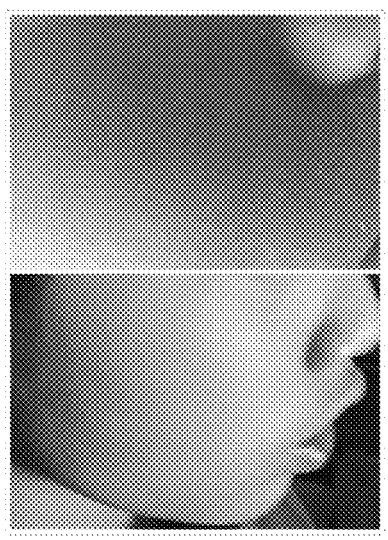
FIG. 24 is a comparison chart showing the effect of the mutant high temperature resistant SOD according to the present invention on the treatment of allergic dermatitis.

Diagnostic criteria: allergic dermatitis is a skin disease caused by allergens, mainly refers to the symptoms of skin such as red and swollen, itching, wheal, peeling when human body is exposed to some allergens (see FIG. 24, the upper picture).

Application method: The product of the invention was applied to the skin surface of the affected area, three times a day, using 7 days for a treatment course.

Efficacy Evaluation Criteria:

Excellent: the skin returns to normal after applying for a week (see FIG. 24, the lower picture).

Improved: 80% of the skin returns to normal.

Invalid: local skin does not meet the criteria of improvement, or no improvement, or even continue to deteriorate.

Result:

| Disease type | Number of patients | Treatment time | Excellent | | Improved | | Invalid | | Total efficacy % |
|---|---|---|---|---|---|---|---|---|---|
| | | | Cases | Excellent % | Cases | Improved % | Cases | Invalid % | |
| allergic dermatitis | 74 | 7 Days | 58 | 78.4% | 14 | 18.9% | 2 | 2.7% | 97.3% |

Conclusion: Inflammation is a defensive response to infection source, trauma or tissue ischemia. The most important and common pathological features of inflammation are the migration, aggregation and infiltration of leukocytes (neutrophils and macrophages). Among them, the chemotaxis, migration and aggregation of the neutrophils is the immune response mechanism of the body in defense of acute injury and inflammatory response, especially when the body's own tissue is damaged or the presence of invasion of foreign objects, this defense is more important.

However, in this defense process (increased vascular permeability, leukocyte migration, aggregation and infiltration), a large number of free radicals are produced causing local oxidation tension. If the oxidation tension cannot be normally removed (decomposition of free radicals), it will cause the body tissue and cell damage (lipid peroxidation, DNA damage, etc.), leading to excessive accumulation of inflammatory cells at the site of injury, resulting in a sustained, severe inflammatory response. Many human diseases have similar characteristics for example mucosal inflammation such as chronic ulcerative colonitis, vaginitis, pharyngitis etc, inflammation caused by exogenous inflammatory factors for example burn, scald, cut, infection or surgery or radiotherapy and chemotherapy etc, and skin inflammation such as tinea manus and pedis, dermatitis, eczema etc.

The occurrence and development of various inflammatory reactions have a common pathology, that is, neutrophil chemotaxis and migration. Therefore, effective inhibition of the chemotaxis and migration of neutrophil to the inflammatory site is a key to effectively screen anti-inflammatory drugs. The invention has successfully constructed a variety of zebrafish inflammatory models and carried out relevant clinical observation experiments. The results showed that the M-type SOD of the invention has a significant therapeutic effect on various inflammations. Meanwhile, the study also revealed the change regulation of neutrophils during inflammation resolution. As described above, such cells are characteristic indicators of many inflammatory responses. The M-type SOD of the present invention achieves an anti-inflammatory effect by removing the oxygen radicals in the process, and thus the M-type SOD provided by the present invention can be effective in treating various Inflammations, such as various mucosal inflammations, inflammation caused by exogenous inflammatory factors or skin inflammation etc.

The invention claimed is:

1. A superoxide dismutase comprising the amino acid sequence of SEQ ID NO:4.

2. A pharmaceutical composition comprising an effective therapeutic amount of the superoxide dismutase according to claim 1.

3. The pharmaceutical composition according to claim 2, wherein the pharmaceutical composition further comprises an antibacterial agent and/or a pharmaceutically acceptable carrier and/or excipient.

4. The pharmaceutical composition according to claim 2, wherein the pharmaceutical composition is in the form of an oral or external dosage form.

5. The pharmaceutical composition according to claim 4, wherein the oral dosage form is an oral solution, a tablet, a pill, a capsule, granules or oral powders.

6. The pharmaceutical composition according to claim 4, wherein the external dosage form is external powders, an ointment, a patch, an external liquid agent, a suppository, a spray, an aerosol, or an inhalant.

7. A cosmetic composition comprising an effective amount of the superoxide dismutase according to claim 1.

8. A food additive comprising the superoxide dismutase according to claim 1.

9. A method of anti-inflammation comprising administrating an effective therapeutic amount of the superoxide dismutase according to claim 1 or a pharmaceutical composition thereof to a subject in need.

10. The method according to claim 9, wherein said inflammation comprises mucosal inflammation, inflammation caused by an exogenous inflammatory factor, or skin inflammation.

11. The method according to claim 10, wherein the mucosal inflammation is inflammation of the respiratory tract, the digestive tract, a reproductive organ, an auditory organ, or a visual organ.

12. The method according to claim 10, wherein the mucosal inflammation is selected from the group consisting of oral ulcer, gingivitis, enteritis, gastritis, vaginitis, pelvic inflammation, cystitis, cervicitis, rhinitis, pharyngitis, otitis media, otitis externa, eye conjunctivitis, and eye keratitis.

13. The method according to claim 10, wherein the exogenous inflammatory factor is selected from the group consisting of bacteria, virus, rickettsia, protozoon, fungi, spirochete and parasite.

14. The method according to claim 10, wherein the exogenous inflammatory factor is selected from the group consisting of mechanical force, high temperature, low temperature, ionizing radiation, and ultraviolet radiation acting on the body.

15. The method according to claim 10, wherein the exogenous inflammatory factor is selected from the group consisting of burn, scald, frostbite, sunburn, cut, radiation damage, surgery and radiotherapy.

16. The method according to claim 10, wherein the exogenous inflammatory factor is selected from the group consisting of radioactive material, strong acid, strong base, strong oxidant, alcohol, and chemical drug.

17. The method according to claim 10, wherein the inflammation is alcohol- or drug-induced hepatitis or inflammation formed after chemotherapy.

18. The method according to claim 10, wherein the skin inflammation is infant eczema.

19. A method of anti-aging or preventing skin pigmentation comprising administrating an effective amount of the superoxide dismutase according to claim 1 or a cosmetic composition thereof to a subject in need.

* * * * *